United States Patent [19]

Taggi

[11] 4,258,190

[45] Mar. 24, 1981

[54] PREPARATION OF ACRIDINONES

[75] Inventor: Arthur J. Taggi, Wilmington, Del.

[73] Assignee: E. I. Du Pont de Nemours and Company, Wilmington, Del.

[21] Appl. No.: 70,834

[22] Filed: Aug. 29, 1979

[51] Int. Cl.³ .......................................... C07D 219/04
[52] U.S. Cl. .................................... 546/103; 560/126
[58] Field of Search .......................... 546/103; 560/126

[56] References Cited

U.S. PATENT DOCUMENTS

| 3,160,510 | 12/1964 | Ehrich | 106/288 |
|---|---|---|---|
| 3,341,345 | 12/1967 | Ehrich | 106/288 |
| 3,748,162 | 7/1973 | West | 106/288 Q |
| 3,947,449 | 3/1976 | Dürckheimer et al. | 546/103 |

*Primary Examiner*—Paul F. Shaver

[57] ABSTRACT

A process for preparing cyclohexanonecarboxylate ester intermediates for the preparation of 1,2,3,4-tetrahydro-7-(phenyl)amino-9(10H)acridinone and 2-(phenyl)amino-9(10H)acridinone and for preparing said acridinones.

18 Claims, No Drawings

PREPARATION OF ACRIDINONES

DESCRIPTION

Technical Field

The present invention relates to 1,2,3,4-tetrahydro-7-(phenyl)amino-9(10H)acridinone, its preparation and its use whereby said tetrahydroacridinone is dehydrogenated in the presence of supported palladium or platinum catalyst to prepare 2-(phenyl)amino-9(10H)-acridinone. More specifically, the present invention relates to 1,2,3,4-tetrahydro-7-(phenyl)amino-9(10H)-acridinone and its preparation from either a 2-cyclohexanonecarboxylate ester or the reaction product of cyclohexanone and an oxalate ester with an alkoxide base, after hydrolysis and decarbonylation to form a 2-cyclohexanonecarboxylate ester by reacting said carboxylate ester with N-phenyl-p-phenylenediamine in the presence of a catalyst to form a phenylaminocyclohexenecarboxylate ester and cyclizing to form 1,2,3,4-tetrahydro-7-(phenyl)amino-9(10H)acridinone.

BACKGROUND ART

U.S. Pat. No. 3,160,510 discloses quinacridonequinone as one component of a solid solution of two or more quinacridone derivatives. Such solid solutions are said to possess enhanced light fastness and tinctorial values. However, as compared to compositions containing quinacridone pigments, compositions containing quinacridonequinone pigments display poor light fastness. U.S. Pat. Nos. 3,341,345 and 3,748,162 disclose colorless quinacridonequinone stabilizers such as N,N'-diphenyl-p-phenylenediamine and 6,13-dihydroquinacridone.

U.S. Ser. No. 969,533, filed Dec. 14, 1978, now abandoned discloses 2-(phenyl)amino-9(10H)acridinone, also named 2-anilinoacridone and 1,2,3,4-tetrahydro-7-(phenyl)amino-9(10H)acridinone, also named 5,6,7,8-tetrahydro-2-anilinoacridone, as stabilizers for quinacridonequinone pigment.

SUMMARY OF THE INVENTION

Now a process has been found for preparing stabilizers for quinacridonequinone pigments. One such stabilizer is 1,2,3,4-tetrahydro-7-(phenyl)amino-9(10H)-acridinone which is also called 5,6,7,8-tetrahydro-2-anilinoacridone.

The 1,2,3,4-tetrahydro-7-(phenyl)amino-9(10H)acridinone can be prepared from 2-cyclohexanonecarboxylate of the formula

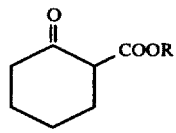

wherein R is an alkyl group of 1-4 carbon atoms.

The 1,2,3,4-tetrahydro-7-(phenyl)amino-9(10H)-acridinone can also be prepared from the aforesaid 2-cyclohexanonecarboxylate ester that has been prepared from the reaction of an oxalate ester and cyclohexanone.

Accordingly, a process for preparing 1,2,3,4-tetrahydro-7-(phenyl)amino-9(10H)acridinone comprises (1) reacting a solution of cyclohexanone and a oxalate ester of the formula

where R is an alkyl group of 1–4 carbon atoms at −20° to 60° C. in the presence of an alkali metal alkoxide and a solvent followed by hydrolysis with aqueous acid to form a 2-cyclohexanoneglyoxylate ester of the formula

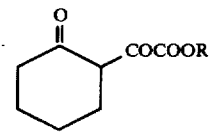

wherein R is as above;

(2) decarbonylating the glyoxylate ester at 110°–200° C. in the presence of an inert high boiling liquid with the optional addition of a catalyst to form the ester of 2-cyclohexanonecarboxylate of the formula

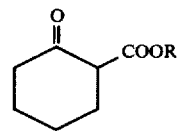

wherein R is as above;

(3) condensing the cyclohexanonecarboxylate ester with N-phenyl-p-phenylenediamine in the presence of a catalytic amount of a strong acid at a temperature of from 80°–150° C. at sufficient pressure to remove by-product water to form 2-{4'-[(phenyl)amino]phenyl}-aminocyclohexenecarboxylate ester of the formula

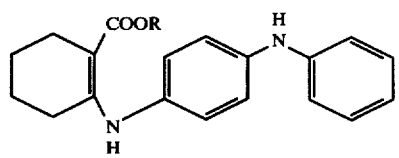

wherein R is as above;

(4) cyclizing the 2-{4'-[(phenyl)amino]phenyl}-aminocyclohexenecarboxylate ester by heating at a temperature of 180°–300° C. in an inert high boiling liquid to obtain 1,2,3,4-tetrahydro-7-(phenyl)amino-9(10H)acridinone also named 5,6,7,8-tetrahydro-2-anilinoacridone of the formula

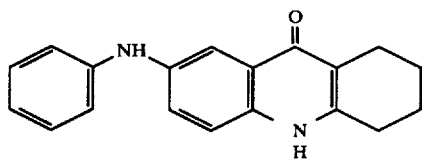

Accordingly, 1,2,3,4-tetrahydro-7-(phenyl)-amino-9(10H)acridinone is prepared by a process comprising (5) condensing 2-cyclohexanonecarboxylate ester of the formula

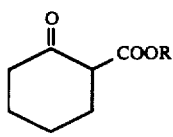

with N-phenyl-p-phenylenediamine in the presence of a catalytic amount of a strong acid at a temperature of from 80°-150° C. at sufficient pressure to remove byproduct water to form a 2-{4'-[(phenyl)amino]phenyl}-aminocyclohexenecarboxylate ester of the formula

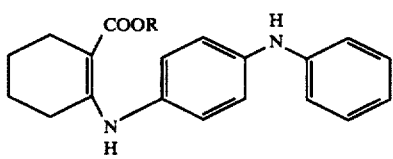

wherein R is as above;

(6) cyclizing the 2-{4'-[(phenyl)amino]phenyl}-aminocyclohexenecarboxylate ester by heating at a temperature of 180°-300° C. in an inert high boiling liquid to obtain 1,2,3,4-tetrahydro-7-(phenyl)amino-9(10H)-acridinone of the formula

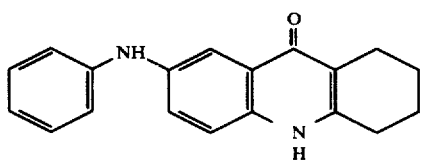

The 1,2,3,4-tetrahydro-7-(phenyl)amino-9(10H)-acridinone of this invention can be converted to another stabilizer for quinacridonequinone pigments, namely 2-(phenyl)-amino-9(10H)acridinone also called 2-anilinoacridone of the formula

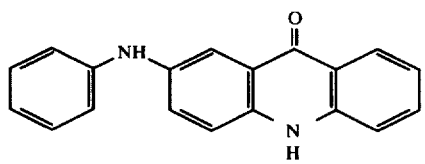

by a process comprising dehydrogenating 1,2,3,4-tetrahydro-7-(phenyl)amino-9(10H)acridinone by heating in an inert high boiling liquid in the presence of a catalytic amount of a supported palladium or platinum catalyst.

The condensation reaction of cyclohexanone and the oxalate ester is conducted in the presence of 1-1.5 equivalents of an alkali metal alkoxide base wherein the alkoxide is 1-4 carbon atoms, in an alcohol or ether solvent at a temperature of −20° C. to 60° C. followed by hydrolysis with aqueous acid to form 2-cyclohexanoneglyoxylate ester. The preferred amount of alkali metal alkoxide base is 1.1-1.2 equivalents.

Representative examples of the alkali metal alkoxides include sodium methoxide, sodium ethoxide, sodium propoxide, sodium isopropoxide, sodium butoxide, potassium methoxide, potassium ethoxide, potassium propoxide, potassium isopropoxide, potassium butoxide, etc. The preferred alkali metal alkoxide base is sodium methoxide because of commercial availability.

The alcohol or ether solvent is an anhydrous low boiling $C_1$-$C_4$ alcohol, an ether, or mixtures thereof, miscible with water. Representative examples of the solvent include methanol, ethanol, propanol, butanol, tetrahydrofuran, ethyleneglycol dimethylether and the like. The preferred solvent is ethanol.

The preferred oxalate ester is diethyl oxalate. The cyclohexanone condensation reaction with the oxalate ester is conducted at a temperature of from −20° C. to 60° C., inclusive, preferably 22°-35° C. for a period of time of 15 minutes to 4 hours in the presence of the aforesaid solvent and the aforesaid alkali metal alkoxide. The solvent is optionally removed, e.g., by vacuum distillation at a temperature of less than 45° C. and the resulting mixture hydrolyzed in the presence of aqueous acid. If the solvent is not removed prior to hydrolysis, the solvent is removed after hydrolysis by extraction. The aqueous layer is then removed and the remaining organic layer washed several times with a salt solution to remove inorganic residues. The organic layer is dried, e.g., by the use of a chemical drying agent such as anhydrous magnesium sulfate, anhydrous calcium sulfate, or anhydrous sodium sulfate, or by vacuum distillation.

Thus, a preferred method of conducting the cyclohexanone condensation reaction is in an anhydrous ethanol solvent with 1.1-1.2 equivalents of sodium methoxide as the alkoxide at a temperature of 22°-35° C. for a period of ½-2 hours. At this point, an inert high boiling liquid made up of an eutectic mixture of 23.5% by weight biphenyl and 76.5% by weight diphenyl oxide known as Dowtherm ® A that is required in later steps is conveniently added. The alcohol is removed by distillation at 30–40 mm Hg pressure at a temperature below 45° C. The remaining mixture is hydrolyzed by the addition of an aqueous sulfuric acid solution in which there is incorporated a salt solution. The salt solution insures that the organic layer will rise to the top of the mixture. The organic layer after separation from the aqueous layer is washed several times with a saturated aqueous sodium chloride solution. The organic layer is then dried by removing water by distillation at 20-30 mm Hg pressure at 60°-90° C. The 2-cyclohexanoneglyoxylate ester produced is a mixture of the methyl and ethyl esters.

The decarbonylation of the 2-cyclohexanoneglyoxylate ester is carried out by heating at 120°-200° C., preferably 140°-150° C. in the presence of an inert high boiling liquid and a catalyst. The inert high boiling liquid is one that will not react with the ester being heated and that has a boiling point above the temperature at which the decarbonylation reaction is run.

Representative examples of said inert high boiling liquid include Dowtherm ® A, dibutyl phthalate, alpha and beta methylnaphthalene, o-dichlorobenzene, p-xylene and the like. The preferred inert high boiling liquid is Dowtherm ® A which is defined above. The inert high boiling liquid selected is conveniently one that may be used in subsequent cyclization and dehydrogenation reactions. Said liquid may be conveniently added in the step before decarbonylation.

The decarbonylation reaction may be conducted in the presence of a catalyst, but a catalyst need not be added. The presence of impurities from the cyclohexanone condensation reaction will catalyze the decarbonylation reaction. However, it is preferred that a catalyst be added to insure a satisfactory reaction since it is possible that said impurities are removed during washing. Additionally, if the 2-cyclohexanoneglyoxylate ester has been isolated and purified, e.g., by distillation, a catalyst must be added.

The catalyst that may be added is a basic organic or inorganic compound. Generally, for reasons of convenience, an inorganic base is preferred. Representative examples of the catalyst that may be added are sodium hydroxide, potassium hydroxide, piperidine, pyrrolidine, diisopropylamine, calcium hydroxide, sodium carbonate, potassium carbonate, the sodium salt of 2-cyclohexanoneglyoxylate ester, the combination of powdered soft glass and powdered iron and the like. The preferred bases are sodium hydroxide, potassium hydroxide and the combination of powdered soft glass and powdered iron. The sodium or potassium hydroxide are conveniently added as aqueous solutions, preferably as 50% by weight aqueous solutions.

The amount of catalyst added is generally from 0.1–5%, preferably 0.2–1% by weight based on the 2-cyclohexanoneglyoxylate.

The decarbonylation may also be conducted by pyrolytic distillation of pure 2-cyclohexanoneglyoxylate in the presence of powdered soft glass and powdered iron as is known in the art.

The condensation of the cyclohexanonecarboxylate ester with N-phenyl-p-phenylenediamine is conducted in the presence of a strong acid catalyst at 80°–150° C. and at a pressure that permits the removal of byproduct water.

Representative examples of the strong acid used are hydrochloric acid, sulfuric acid, p-toluenesulfonic acid, benzenesulfonic acid, trifluoroacetic acid, naphthalenesulfonic acid, toluenesulfonic acid, picric acid, o-phosphoric acid, pyrophosphoric acid, and the like.

If a volatile acid is used, e.g., trifluoroacetic acid, an amine such as N-methylaniline may be added but is not required. The use of such an amine may tend to help reduce the loss of the volatile acid catalyst.

Generally, byproduct water is removed by vacuum distillation.

The condensation of the 2-cyclohexanonecarboxylate esters of this invention to form the 2-{4'-[(phenyl)amino]phenyl}aminocyclohexenecarboxylate ester can also be carried out by starting with a pure form of the carboxylate esters that have been prepared and isolated according to procedures in the prior art. In such a case, the pure carboxylate ester in a solvent, e.g., benzene or toluene, is condensed with N-phenyl-p-phenylenediamine in the presence of a strong acid catalyst and the byproduct water removed by azeotropic distillation. However, before proceeding to cyclization, the solvent must be removed, e.g., by vacuum distillation. Also, the pure isolated carboxylate esters may be condensed with N-phenyl-p-phenylenediamine in an inert high boiling liquid, e.g., Dowtherm ® A at reduced pressure and with an acid catalyst. Alternatively, the condensation reaction is carried out with the decarbonylation reaction product contained in an inert high boiling liquid. If the 2-cyclohexanonecarboxylate is a mixture of esters the resulting 2-{4'-[(phenyl)amino]phenyl}aminocyclohexenecarboxylate will also be a mixture of esters.

The cyclizing of the 2-{4'-[(phenyl)amino]phenyl}-aminocyclohexenecarboxylate is carried out by heating a solution of the cyclohexene in an inert high boiling solvent at 180°–300° C. with the removal of byproduct alcohol. The product formed is 1,2,3,4-tetrahydro-7-(phenyl)amino-9(10H)acridinone which is isolated in high purity by filtration of the reaction mixture after cooling and washing with an appropriate solvent, for example, methanol, ethanol, isopropanol, propyl alcohol, acetone, methyl ethyl ketone, tetrahydrofuran, etc.

The product 1,2,3,4-tetrahydro-7-(phenyl)amino-9(10H)acridinone is useful as a stabilizer for quinacridonequinone pigments.

The inert high boiling liquid for the hereinbefore described decarbonylation reaction and cyclization reaction and the dehydrogenation reaction described hereinafter is any inert liquid whose boiling point lies above the temperature at which the particular reaction is run, but not so high as to preclude its removal from the reaction mixture by distillation at reasonable temperatures. Representative examples of the inert high boiling liquid are α-methylnaphthalene, β-methylnaphthalene, biphenyl, diphenyl oxide, Dowtherm ® A, diethyl phthalate and mineral oils that boil within the range 180°–300° C. It is convenient to use the same inert high boiling liquid used in the decarbonylation reaction in the cyclization and dehydrogenation reaction.

The preferred mode of the cyclizing reaction involves adding the reaction product comprising the cyclohexene and the preferred inert liquid, Dowtherm ® A, to refluxing Dowtherm ® A at 256°–258° C. in a stirred vessel. Nitrogen is passed over the mixture to remove alcohol vapors that are produced. Product precipitates during the reaction and may be isolated by cooling and filtering followed by washing with methanol.

The dehydrogenation reaction is carried out by heating the tetrahydroacridinone as a suspension or a solution in an inert high boiling liquid in the presence of a supported palladium or platinum catalyst. The dehydrogenation catalyst of this invention is limited to supported palladium or platinum. The dehydrogenation catalyst is critical in achieving a product that can be prepared in a reasonable reaction time. Palladium is preferred because it yields the highest purity product.

The support for the catalyst may be selected from any known support materials such as carbon, silicon carbide, silica, alumina, aluminosilicates, inorganic silicates, inorganic carbonates, pumice, montmorillonite and the like that are stable under the reaction conditions. The preferred support materials are alumina and carbon. Generally, the form of the support can be powdered, granular or pelletized. Most preferred are alumina pellets due to commercial availability and ease in removal from the product slurry. Carbon powder supported catalysts are especially preferred because they give higher reaction rates and yield higher purity products.

The amount of supported catalyst based on the tetrahydroacridinone can vary widely and depends on the support chosen. Generally, from 0.1–200% by weight of supported catalyst based on the tetrahydroacridinone is used depending on the support. Generally 20–90% by weight based on the tetrahydroacridinone, preferably 40–90%, of the supported catalyst is used when the support is alumina pellets. Generally, 0.1–10% by weight based on the tetrahydroacridinone, preferably 0.2–5% of the supported catalyst is used when the support is carbon powder.

The amount of platinum or palladium on the support generally varies from 0.1–15% by weight based on the weight of support depending on the support. Generally, 0.1–5% by weight of platinum or palladium based on the weight of alumina pellets, preferably 0.4–1%, or 2–15% by weight platinum or palladium based on the weight of carbon powder, preferably 5–10% is used.

In general, the higher the temperature at which the dehydrogenation is run, the greater the reaction rate. Generally, the dehydrogenation reaction is carried out at 180°–350° C., preferably 230°–300° C. The reaction may be run under pressure to increase the reaction temperature. Pressures from 1 atm to 20 atm are generally operable.

Dowtherm ® A is the preferred medium for the dehydrogenation reaction because of its high boiling point and because the desired product precipitates when the medium is cooled. This permits easy isolation of the product.

The cyclization and dehydrogenation reactions may be combined for efficiency of operation by adding the catalyst for dehydrogenation to the refluxing mixture after cyclization without isolation of the tetrahydroacridinone formed in cyclization. Alternatively, the cyclohexene ester can be added to a refluxing, high boiling inert solvent containing the dehydrogenation catalyst to carry out the cyclization and the dehydrogenation in one step.

The product of the process of the invention, namely, 2-(phenyl)amino-9(10H)acridinone is also useful as a stabilizer for quinacridonequinone pigments.

The process of this invention, among other things, results in the preparation of 2-(phenyl)amino-9(10H)acridinone and 1,2,3,4-tetrahydro-7-(phenyl)amino-9(10H)acridinone of high purity. The process of this invention achieves this high purity by simply washing the anilinoacridinones with a solvent such as methanol, ethanol, isopropanol and the like. The same high purity of said anilinoacridinones is obtained even when the process of the invention is run without isolating and purifying the intermediates involved.

EXAMPLES

In the following examples provided to further illustrate the invention, all percentages are by weight unless otherwise indicated.

EXAMPLE 1

Preparation of 2-(phenyl)amino-9(10H)acridinone from cyclohexanone without isolating intermediates Sodium methoxide (25 g, 0.46 mol) was dissolved in 139 ml of anhydrous ethanol in a mechanically stirred flask equipped with a nitrogen atmosphere. The solution was allowed to cool to room temperature. A mixture of 41.7 g (0.43 mol) of cyclohexanone and 67.5 g (0.46 mol) of diethyl oxalate was added slowly such that the reaction temperature did not exceed 35°. The mixture was stirred at room temperature for 4 hours. Dowtherm ® A (236 ml) was added. The alcohol was removed by distillation at 30 mm Hg until the reaction temperature rose to 28° C. The thick slurry was acidified with a mixture of 26.5 g of sodium chloride, 145 ml of water and 45 ml of a 75 volume percent acetic acid solution. The layers were separated and the Dowtherm ® A layer was washed twice with 150 ml each of saturated sodium chloride solution. Water was removed from the Dowtherm ® A solution by distillation at 75°–85° C. and 25 mm Hg for 30 minutes.

A trace of iron powder was added to the reaction mixture and it was held at 145° for 2½ hours to effect decarbonylation.

The mixture was cooled to 50° C. and 66.5 g (0.36 mol) of N-phenyl-p-phenylenediamine and 0.8 ml of trifluoroacetic acid were added. The reaction mixture was heated at 85° C. and 25 mm Hg for 1 hour, then 125° C. and 25 mm Hg for ½ hour. The solution was allowed to cool. It was then filtered.

The filtrate was added over 20 minutes to 167 ml of refluxing Dowtherm ® A in a resin kettle equipped with a nitrogen flow and a steam heated condenser, and containing 40 g of 0.5% palladium on ⅛" alumina pellet catalyst contained in a stainless steel mesh basket. The addition was done in such a way as to maintain the reaction temperature over 250° C. The reaction was held at reflux for 20 hours. The basket was raised and the mixture cooled to 80° C. The precipitated solids were filtered and washed well with methanol. Vacuum oven drying overnight gave 47.8 g (39.4% yield based on cyclohexanone) of 2-(phenyl)amino-9(10H)acridinone as bright yellow platelets.

EXAMPLE 2

Preparation of mixed methyl and ethyl esters of 2-{4'-[(phenyl)amino]phenyl}aminocyclohexenecarboxylate from the mixed methyl and ethyl esters of 2-cyclohexanonecarboxylate A solution of 18.4 g (0.1 mol) of N-phenyl-p-phenylenediamine, 18.0 g (0.11 mol) of 2-cyclohexanone carboxylate (effective molecular weight 164 based on 60% ethyl 40% methyl, Aldrich Chemical Co.), 0.4 ml of trifluoroacetic acid and 600 ml of toluene was refluxed for ¾ hour in a flask equipped with a Dean-Stark azeotropic water separator. The mixture was cooled and the solvent removed under vacuum. The resultant dark oil was dissolved in ether and was treated with decolorizing carbon. The mixture was filtered and the solvent was removed in vacuo. The resultant oil was dissolved in the minimum amount of methanol. The solution was seeded and chilled in ice. The resultant off-white crystals were collected by filtration and were washed three times with petroleum ether to give 23.2 g (70% yield) of 2-{4'-[(phenyl)amino]phenyl}aminocyclohexenecarboxylate. This process was repeated in substantially the same way and the material prepared had mp 74°–78° and an infrared spectrum (Nujol mull) with major bands at 3420 (NH) and 1650 (ester C=O) $cm^{-1}$.

EXAMPLE 3

Preparation of 1,2,3,4-tetrahydro-7-(phenyl)amino-9(10H)acridinone from 2-{4'-[(phenyl)amino]phenyl}aminocyclohexenecarboxylate ester One hundred ml of Dowtherm ® A (an eutectic mixture of biphenyl and diphenyl ether) was heated to reflux (256° C.) and purged with nitrogen in a magnetically stirred flask with a steam-heated condenser. A solution of 10 g of a mixture of the methyl and ethyl esters of 2-{4'-[(phenyl)amino]phenyl}aminocyclohexenecarboxylate and 150 ml of Dowtherm ® A was added over 1 hour. A precipitate was formed during the reaction. The mixture was refluxed for 1 hour after the addition was complete. The mixture was cooled. Petroleum ether was added to speed filtration and the precipitated solid isolated by filtration. The precipitate was washed thoroughly with petroleum ether and then was vacuum oven dried at 80° overnight to give 7.8 g (89% yield) of a cream-colored solid of 1,2,3,4-tetrahydro-7-(phenyl)amino-9(10H)acridinone.

This process was repeated in substantially the same way and the material prepared had mp >300° C. and an infrared spectrum (Nujol mull) with characteristic bands at 3390 (NH) and three bands in the region 1580–1620 cm$^{-1}$.

EXAMPLE 4

Preparation of 2-(phenyl)amino-9(10H)acridinone by dehydrogenation

A mixture of 2 g of 1,2,3,4-tetrahydro-7-(phenyl)amino-9(10H)acridinone, 100 mg of 10% palladium on activated charcoal and 100 ml of Dowtherm ® A was refluxed at 256° C. with stirring in a nitrogen atmosphere. After 1¼ hours at reflux, the mixture was cooled. Product precipitated. Petroleum ether was added to speed filtration and the product was collected on a funnel. The product was washed with petroleum ether. The product was dissolved in N,N-dimethylformamide and filtered to remove the catalyst. The filtrate was diluted with water to precipitate the product. The product was filtered and washed with water. Vacuum drying at 80° C. overnight gave 1.83 g (93% yield) of the bright yellow product, 2-(phenyl)amino-9(10H)acridinone.

An infrared spectrum of material prepared in essentially the same way was superimposable on a spectrum of material prepared according to the method described in L. Calb, *Ber., Deut. Chem. Gess.* 43, 2213 (1910).

EXAMPLE 5

Preparation of 2-(phenyl)amino-9(10H)acridinone from 2-{4'-[(phenyl)amino]phenyl}aminocyclohexenecarboxylate ester mixture, without isolating intermediates Dowtherm ® A (100 ml) was brought to reflux in a mechanically stirred flask with a steam-heated condenser and nitrogen atmosphere. A solution of 30 g of a mixture of the methyl and ethyl esters of 2-{4'-[(phenyl)amino]phenyl}aminocyclohexenecarboxylate in 300 ml of Dowtherm ® A was added dropwise over 2 hours. Reflux was continued for ½ hour after the addition was complete. The reaction was cooled slightly and 1.5 g of 10% palladium on carbon was added. The mixture was refluxed for an additional 6 hours. The mixture was cooled. The precipitate that formed was filtered. The precipitate was washed with petroleum ether. The precipitate was dissolved in 150 ml of warm dimethylformamide (DMF). The DMF solution was filtered and the solid remaining on the funnel was washed with an additional 75 ml of DMF. The combined DMF filtrates were diluted to 2 liters with water. The product precipitated and was collected on a funnel and was washed well with water. Vacuum oven drying at 80° C. for 2 days gave 25 g (96% yield) of 2-(phenyl)amino-9(10H)acridinone.

EXAMPLE 6

Decarbonylation of 2-cyclohexanoneglyoxylate ester mixture in solution

Ten grams of a mixture of the methyl and ethyl esters of 2-cyclohexanoneglyoxylate prepared as described in H. R. Snyder, L. A. Brooks and S. H. Shapiro, *Organic Synthesis Collective Vol. II,* 531, 0.1 g of powdered soft glass, a trace of iron powder and 75 ml of Dowtherm ® A were heated to 200° C. in a nitrogen atmosphere, with stirring. Gas evolution stopped after 2 hours at 200° C. Thin layer chromatographic analysis (silica gel plates, eluted with 10 parts hexane:1 part acetone then stained with a solution of ferric chloride in ethanol) showed complete conversion to 2-cyclohexanonecarboxylate ester mixtures (wherein R was methyl and ethyl).

EXAMPLE 7

Preparation of 2-(phenyl)amino-9(10H)acridinone from 2-cyclohexanonecarboxylate ester without isolating intermediates A solution of 18.6 g (0.1 mol) of practical grade N-phenyl-p-phenylenediamine, 18.0 g (0.11 mol) of a mixture of the methyl and ethyl esters of 2-cyclohexanonecarboxylate (Aldrich Chemical Co., 40% methyl, 60% ethyl), 0.2 ml of trifluoroacetic acid and 600 ml of toluene was refluxed in a flask equipped with a Dean-Stark azeotropic water separator for 1 hour. The solvent was removed under vacuum. The resultant dark oil was dissolved in 200 ml of warm Dowtherm ® A and was added dropwise over 1 hour to 90 ml of refluxing Dowtherm ® A which was contained in a flask equipped with a steam-heated condenser, nitrogen flow and a mechanical stirrer. Heating was continued for 1 hour after the addition was complete. 1.45 g of 10% palladium on carbon was added and the mixture was refluxed for an additional 13 hours. The mixture was cooled and the solids that precipitated were collected on a funnel. The solids were washed with four 75 ml aliquots of methanol. The solids were dissolved in warm DMF and filtered to remove catalyst. The DMF filtrate was diluted with water to precipitate product. The product was collected on a funnel and washed well with water. Drying in a vacuum oven at 120° C. overnight gave 24.54 g (86% yield) of product 2-(phenyl)amino-9(10H)acridinone.

EXAMPLE 8

Best Mode Starting with Carboxylate Esters

Preparation of 1,2,3,4-tetrahydro-7-(phenyl)amino-9(10H)acridinone from 2-cyclohexanonecarboxylate ester in Dowtherm ® A A mixture of 18.4 g (0.1 mol) of N-phenyl-p-phenylenediamine, 18.0 g (0.11 mol) of a mixture of the methyl and ethyl esters of 2-cyclohexanonecarboxylate (Aldrich Chemical Co., 40% methyl, 60% ethyl ester), 0.2 ml of trifluoroacetic acid and 100 ml of Dowtherm ® A was heated and stirred at 85°–90° and 25 mm Hg for 1 hour, then at 115°–120° and 25 mm Hg for ½ hour. The resultant solution was cooled to room temperature and was transferred to a dropping funnel using 25 ml of Dowtherm ® A to wash the glassware. This solution was added dropwise over 1 hour to 25 ml of refluxing Dowtherm ® A in a mechanically stirred flask equipped with a steam heated condenser. Heating was continued for 1 hour after the addition was complete. The mixture was cooled to room temperature and the precipitated product was collected by filtration. The product was washed well with four 50 ml aliquots of methanol. Vacuum oven drying at 80° C. overnight gave 22.6 g (78% yield) of the product 1,2,3,4-tetrahydro-7-(phenyl)amino-9(10H)acridinone.

EXAMPLE 9

Preparation of
1,2,3,4-tetrahydro-7-(phenyl)amino-9(10H)acridinone
from 2-cyclohexanonecarboxylate ester A mixture of 73.6 g (0.4 mol) of N-phenyl-p-phenylenediamine, 72 g (0.4 mol) of a mixture of the methyl and ethyl esters of 2-cyclohexanonecarboxylate (Aldrich Chemical Co., 40% methyl, 60% ethyl ester) 0.8 ml of trifluoroacetic acid and 1200 ml of toluene was refluxed for 1 hour in a flask equipped with a Dean-Stark water separator. The solvent was removed under vacuum and the resultant oil was dissolved in 500 ml of Dowtherm ® A. This solution was added over 1 hour to 100 ml of refluxing Dowtherm ® A in a flask equipped with mechanical stirrer, nitrogen flow and a steam heated condenser. Reflux was continued for 1 hour after the addition was complete. The mixture was cooled to room temperature and the precipitated product was filtered. The product was washed with four 200 ml aliquots of methanol. Vacuum oven drying at 80° C. overnight gave 99.9 g (89% yield) of 1,2,3,4-tetrahydro-7-(phenyl)amino-9(10H)acridinone. The product was identified by microanalysis.

Anal. calc'd for $C_{19}H_{18}N_2O$: C, 78.59; H, 6.24; N, 9.65. Found: C, 78.37; H, 6.11; N, 9.77. C, 78.41; H, 6.42; N, 9.85.

EXAMPLE 10

Preparation of 2-(phenyl)amino-9(10H)acridinone from 1,2,3,4-tetrahydro-7-(phenyl)amino-9(10H)acridinone A mixture of 70 g of 1,2,3,4-tetrahydro-7-(phenyl)amino-9(10H)acridinone and 700 ml of Dowtherm ® A was brought to reflux in a 2 liter resin kettle, in a nitrogen atmosphere. A stainless steel mesh basket containing 14.5 g of 0.5% palladium on ⅛ inch alumina pellets was lowered into the reaction mixture. The mixture was refluxed for 18 hours. The basket was removed from the reaction mixture, which was then allowed to cool. The precipitated product was collected on a filter and was washed with four 350 ml aliquots of methanol. Vacuum oven drying at 100° C. overnight gave 61.4 g (89%) of the product that was analyzed by microanalysis.

Anal. calc'd for $C_{19}H_{14}N_2O$: C, 79.69; H, 4.93; N, 9.78. Found: C, 78.85; H, 4.91; N, 9.61. C, 78.76; H, 5.14; N, 9.60.

EXAMPLE 11

Best Mode for the Preparation of
1,2,3,4-tetrahydro-7-(phenyl)amino-9(10H)acridinone
from cyclohexanone, without isolating intermediates A mixture of 139 ml of absolute ethanol, 25 g of sodium methoxide and 67.5 g of diethyloxalate was prepared in a mechanically stirred 1 liter flask under nitrogen atmosphere. The mixture was cooled to 22° C. Cyclohexanone (41.7 g) was added dropwise, keeping the temperature below 35°. The mixture was stirred for ½ hour at room temperature, then 236 ml of Dowtherm ® A were added. The alcohol was removed by distillation at 35 mm Hg until the reaction mixture temperature reached 29°. The mixture was hydrolyzed by adding a solution of 24 g of concentrated sulfuric acid, 216 ml of water and 9 g of sodium chloride. An additional 3 g of sodium chloride were added to speed separation of the layers. The layers were separated and the organic layer was washed three times with saturated aqueous sodium chloride. The organic layer was then dehydrated by distillation at 25 mm Hg and 65° for ¾ hour. A 50% aqueous solution of sodium hydroxide (0.6 g) was added and the mixture heated at 145° for 2.5 hours to effect decarbonylation. An infrared spectrophotometric analysis of the reaction mixture showed 0.311 mole of 2-cyclohexanonecarboxylate ester. One equivalent (57.20 g) of N-phenyl-p-phenylenediamine and 0.8 ml of trifluoroacetic acid were added. The solution was heated at 85° and 25 mm Hg pressure for 1 hour, then 125° and 25 mm Hg for ½ hour to bring about condensation. This solution was then added dropwise to 176 ml of refluxing Dowtherm ® A in a mechanically stirred flask with a nitrogen sweep through the flask and a steam heated condenser. The addition was adjusted such that the reaction temperature did not drop below 250° C. Reflux was continued for 1 hour after the addition was complete. The mixture was cooled to 90°–100° and filtered to isolate the product. The filter cake was washed well with methanol and was dried in a vacuum oven to give 66.75 g (54%, corrected for loss of product due to above IR sample) of 1,2,3,4-tetrahydro-7(phenyl)amino-9(10H)acridinone.

EXAMPLE 12

Preparation of
1,2,3,4-tetrahydro-7-(phenyl)amino-9(10H)acridinone
from cyclohexanone, without isolating intermediates.
No decarbonylation catalysts used Sodium methoxide (25 g, 0.46 mol) and 67.5 g of diethyl oxalate (0.46 mol) were dissolved in 139 ml of anhydrous alcohol in a mechanically stirred flask equipped with a nitrogen atmosphere. The solution was allowed to cool to 22°. Cyclohexanone (41.7 g, 0.43 mol) was added at a rate such that the reaction temperature did not exceed 35°. The mixture was then stirred overnight at room temperature. Dowtherm ® A (236 ml) was added and the mixture was distilled at 25 mm Hg until the reaction temperature reached 29°. The resultant slurry was hydrolyzed by adding a mixture of 26.5 g of sodium chloride and 45 ml of 75 volume percent aqueous acetic acid in 145 ml of water. An additional 48 ml of water was added to speed the separation. The layers were separated and the Dowtherm ® A layer was washed twice, each time with half of a solution of 90 g of sodium chloride in 250 ml of water (a saturated solution). The aqueous layers were discarded.

Water was removed from the Dowtherm ® A layer by vacuum distillation at 65° and 25 mm Hg for ½ hour. Vacuum was removed and the solution was heated to 145° for 2.5 hours to bring about decarbonylation. No additional catalysts were used.

N-phenyl-n-phenylenediamine (66.5 g, 0.36 mol) and 0.8 ml of trifluoroacetic acid were added. The reaction mixture was heated at 85° C. and 25 mm Hg for 1 hour, then at 125° C. and 25 mm Hg for ½ hour. The mixture was filtered, using 30 ml of fresh Dowtherm ® A to wash the glassware. The solution was placed in a dropping funnel and added dropwise to 75 ml of vigorously refluxing (256°) Dowtherm ® A in a mechanically stirred flask equipped with a nitrogen purge and a steam heated condenser. The material was added over 1½ hours. Refluxing was continued for 1 hour after the addition was complete. The mixture was cooled and the precipitated product was isolated by filtration. The product was washed well with methanol and vacuum oven dried to give 61.2 g (50% yield) of the acridinone compound indicated above. This yield is corrected for in-process samples taken.

EXAMPLE 13

Best Mode Starting With Cyclohexanone

Preparation of 2-(phenyl)amino-9(10H)acridinone using caustic as the decarbonylation catalyst A solution of sodium methoxide (25 g, 0.46 mol), diethyl oxalate (67.5 g, 0.46 mol) and 139 ml of anhydrous ethanol was prepared in a mechanically stirred flask under a nitrogen atmosphere. The solution was cooled to 22°. Cyclohexanone (41.7 g, 0.43 mol) was added at a rate such that the reaction temperature did not exceed 35°. The mixture was stirred for ½ hour, then 236 ml of Dowtherm ® A was added. Alcohol was distilled out at 35 mm until the reaction temperature reached 29°. The mixture was hydrolyzed by addition of a solution of 17.1 g of sodium chloride, 41 ml of a 75% (v/v) solution of acetic acid and 192 ml of water. The layers were separated and the Dowtherm ® A layer was washed three times with 125 ml portions of saturated sodium chloride. An emulsion in the last salt wash was broken by filtration. The reaction mixture was dewatered by distillation at 65° and 25 mm Hg for ¾ hour. Sodium hydroxide (0.6 g of a 50% aqueous solution) was added and the mixture heated at 145° for 2.5 hours. An infrared analysis showed 0.336 mol of 2-cyclohexanonecarboxylate ester present. One equivalent (61.8 g) of N-phenyl-p-phenylenediamine and 0.8 ml of trifluoroacetic acid were added. The mixture was heated at 85° and 25 mm Hg for 1 hour, then 125° and 25 mm Hg for ½ hour. This amine solution was added slowly to 176 ml of refluxing Dowtherm ® A, containing 2 g of 10% palladium on charcoal catalyst. The Dowtherm ® A/palladium suspension was contained in a mechanically stirred flask with a nitrogen atmosphere and a steam heated condenser. The rate of addition of the amine solution was such that the pot temperature remained over 250°. Reflux was continued for 8 hours. The mixture was cooled. The resulting precipitate was washed well with methanol. The precipitate was dissolved in 300 ml of warm dimethylformamide. This solution was filtered to remove the catalyst. The filtrate was poured into 3 liters of water. The precipitated product was filtered and was washed with water and was vacuum oven dried to give 52.7 g, 43% yield of the acridinone indicated above, corrected for samples removed.

EXAMPLE 14

Best Mode for dehydrogenation of 1,2,3,4-tetrahydro-7-(phenyl)amino-9(10H)acridinone The following ingredients
8.2 g of 10% Pd on carbon
164.3 g of 1,2,3,4-tetrahydro-7-(phenyl)amino-9(10H)acridinone
1400 ml of Dowtherm ® A (as defined hereinbefore)
were placed in a 3.5 l reactor, equipped with an external heater and a condenser, agitator, nitrogen purge means and a discharge line with an internal filter of 0.5 micron pore size leading to a receiver. The reactor was heated and the contents refluxed for 2½ hours under a nitrogen purge at about 250° C. and 1 atmosphere of pressure. The contents of the reactor were filtered via the discharge line by pressurizing the reactor to 29 psig to push the contents through the filter in the discharge line into the receiver leaving the catalyst and a small heel in the reactor. The yield of 2-(phenyl)amino-9(10H)acridinone was 82.5% by weight.

The above was repeated using the same amounts of the same ingredients except that 1.2 g of the catalyst were added to the heel of the above run. Four runs gave yield of 89.5%, 94.4%, 93.7% and 95.2%.

COMPARATIVE EXAMPLES A-I

The process of Example 4 was repeated except that the catalyst, support and starting material shown in the table below were used. Analysis of the reaction mixture by thin layer chromatography indicated that in all cases there was considerable starting material in the reaction mixture and only a small amount of 2-(phenyl)amino-9(10H)acridinone. Therefore, none of the base metal catalysts shown were considered useful to dehydrogenate 1,2,3,4-tetrahydro-7-(phenyl)amino-9(10H)acridinone.

| DEHYDROGENATION | | | |
|---|---|---|---|
| Comparative | Catalyst | | |
| Examples | Metal | Support | Amount |
| A | — | $Al_2O_3$ fumed | 2.5 g |
| B | — | $Al_2O_3$ pellets | 5 g |
| C | $MnO_2$ | — | 0.25 g |
| D | NiO (15%) | $Al_2O_3$ pellets | 1 g |
| E | $Cr_2O_3$ (7.5% Cr) | $Al_2O_3$ pellets | 1 g |
| F | $Fe_2O_3$ (20%) | $Al_2O_3$ pellets | 1 g |
| G | Ni (60% Ni) | kieselguhr | 0.5 g |
| H | $MoO_3$ (10-20% Mo) | $Al_2O_3$ pellets | 5 g |
| I | — | Davison 4A Molecular sieves | 0.23 g |

| Com. parative Examples | 1,2,3,4-Tetrahydro-7-(phenyl)amino-9(10H)acridinone Amount | Dowtherm ® A Amount | 2-(Phenyl)-amino-9(10H)-acridinone Amount |
|---|---|---|---|
| A | 2.5 g | 25 ml | Trace |
| B | 5 g | 50 ml | Trace |
| C | 2.5 g | 25 ml | Trace |
| D | 2 g | 50 ml | Trace |
| E | 2 g | 50 ml | Trace |
| F | 2 g | 50 ml | Trace |
| G | 2 g | 50 ml | Trace |
| H | 5 g | 50 ml | Trace |
| I | 1 g | 50 ml | Trace |

INDUSTRIAL APPLICABILITY

The process of the invention permits the preparation of intermediates for the preparation of stabilizers for quinacridonequinone pigments. The stabilizers prepared include the compounds 2-(phenyl)amino-9(10H)acridinone and 1,2,3,4-tetrahydro-7-(phenyl)amino-9(10H)acridinone.

I claim:
1. A process which comprises
(a) reacting a solution of cyclohexanone and oxalate ester of the formula

where R is an alkyl group of 1-4 carbon atoms at from −20° C. to 60° C. in the presence of an alkali metal alkoxide and a solvent and then hydrolyzing the reaction product with an aqueous acid to form a 2-cyclohexanoneglyoxylate ester of the formula

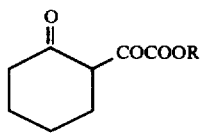

wherein R is as above; and (b) decarbonylating the glyoxylate ester at 110°–200° C. in the presence of an inert high boiling liquid with the optional addition of a catalyst to form 2-cyclohexanonecarboxylate ester of the formula

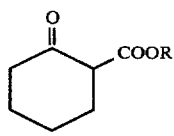

wherein R is as above.

2. The process of claim 1 wherein in (a) the oxalate ester is diethyl oxalate, the alkoxide is sodium methoxide and the solvent is ethanol.

3. The process of claim 1 wherein in (b) a catalyst is added.

4. The process of claim 3 wherein the catalyst is sodium hydroxide and the inert high boiling liquid is an eutectic mixture of 23.5% by weight biphenyl and 76.5% by weight diphenyl oxide.

5. The process of claim 3 wherein the catalyst is potassium hydroxide.

6. The process of claim 3 wherein soft glass and iron powder are the catalyst.

7. A process which comprises (a) reacting a solution of cyclohexanone and oxalate ester of the formula

where R is an alkyl group of 1–4 carbon atoms at from −20° C. to 60° C. in the presence of an alkali metal alkoxide and a solvent and then hydrolyzing the reaction product with an aqueous acid to form a 2-cyclohexanoneglyoxylate ester of the formula

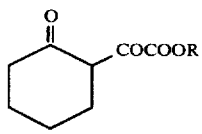

wherein R is as above; and (b) decarbonylating the glyoxylate ester at 110°–200° C. in the presence of an inert high boiling liquid with the optional addition of a catalyst to form 2-cyclohexanonecarboxylate ester of the formula

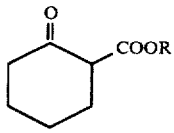

wherein R is as above (c) condensing the cyclohexanonecarboxylate ester with N-phenyl p-phenylenediamine in the presence of a catalytic amount of a strong acid at a temperature of from 80°–150° C. at sufficient pressure to remove byproduct water to form a 2-{4′-[(phenyl)amino]phenyl}aminocyclohexenecarboxylate ester of the formula

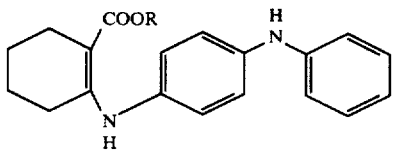

wherein R is as above; and (d) cyclizing the 2-{4′-[(phenyl)amino]phenyl}-aminocyclohexenecarboxylate ester by heating at a temperature of 180°–300° C. in an inert high boiling liquid to obtain 1,2,3,4-tetrahydro-7-(phenyl)amino-9(10H)acridinone of the formula

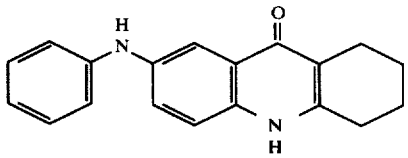

8. The process of claim 7 wherein in (c) the strong acid is trifluoroacetic acid.

9. The process of claim 7 wherein in (d) the inert high boiling liquid is an eutectic mixture of 23.5% by weight biphenyl and 76.5% by weight diphenyl oxide.

10. The process of claim 7 wherein the tetrahydroacridinone is dehydrogenated by heating in an inert high boiling liquid at 180°–350° C. and 1–20 atmospheres pressure in the presence of a catalytic amount of a supported palladium or platinum catalyst to produce 2-(phenyl)amino-9(10H)acridinone of the formula

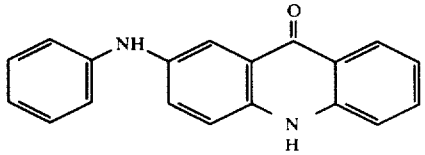

11. The process of claim 10 wherein the catalyst is palladium.

12. The process of claim 10 wherein the support is alumina.

13. The process of claim 10 wherein the support is carbon.

14. The process of claim 10 wherein the inert high boiling liquid is an eutectic mixture of 23.5% by weight of biphenyl and 76.5% by weight of diphenyl oxide.

15. A process for preparing 1,2,3,4-tetrahydro-7-(phenyl)amino-9(10H)acridinone which comprises (a) condensing 2-cyclohexanonecarboxylate ester of the formula

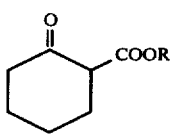

with N-phenyl-p-phenylenediamine in the presence of a catalytic amount of a strong acid at a temperature of from 80°-150° C. at sufficient pressure to remove byproduct water to form a 2-{4'-[(phenyl)amino]phenyl}aminocyclohexanecarboxylate ester of the formula

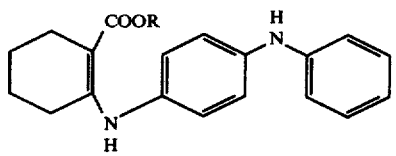

wherein R is as above;

(b) cyclizing the 2-{4'-[(phenyl)amino]phenyl}-aminocyclohexenecarboxylate ester by heating at a temperature of 180°-300° C. in an inert high boiling liquid to obtain 1,2,3,4-tetrahydro-7-(phenyl)amino-9(10H)-acridinone of the formula

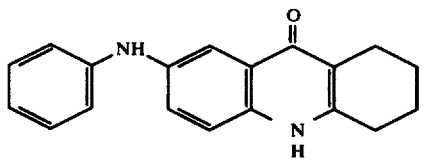

16. The process of claim 15 wherein the tetrahydroacridinone is dehydrogenated by heating in an inert high boiling liquid at 180°-350° C. and 1-20 atmospheres pressure in the presence of a catalytic amount of a supported palladium or platinum catalyst to produce 2-(phenyl)amino-9(10H)acridinone of the formula

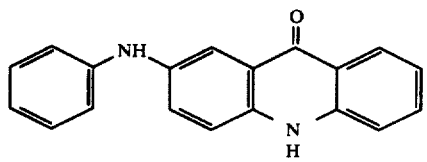

17. As a composition of matter, an acridinone of the formula

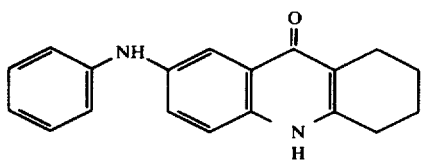

18. A process for dehydrogenating 1,2,3,4-tetrahydro-7-(phenyl)amino-9(10H)acridinone of the formula

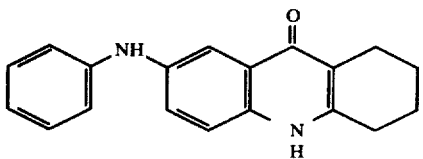

by heating in an inert high boiling liquid at 180°-350° C. and 1-20 atmospheres pressure in the presence of a catalytic amount of a supported palladium or platinum catalyst to produce 2-(phenyl)amino-9(10H)-acridinone of the formula

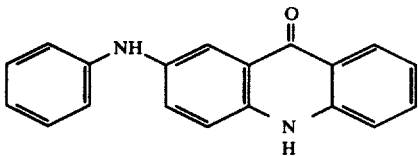

* * * * *